United States Patent
Kriss

(10) Patent No.: US 10,337,964 B2
(45) Date of Patent: Jul. 2, 2019

(54) SYSTEMS AND METHODS FOR MONITORING, INFERRING STATE OF HEALTH, AND OPTIMIZING EFFICIENCY OF REFRIGERATION SYSTEMS

(71) Applicant: KLATU Networks, LLC, Poulsbo, WA (US)

(72) Inventor: Richard Kriss, Poulsbo, WA (US)

(73) Assignee: KLATU Networks, Inc., Poulsbo, WA (US)

( * ) Notice: Subject to any disclaimer, the term of this patent is extended or adjusted under 35 U.S.C. 154(b) by 726 days.

(21) Appl. No.: 14/275,771

(22) Filed: May 12, 2014

(65) Prior Publication Data

US 2014/0324388 A1    Oct. 30, 2014

Related U.S. Application Data

(63) Continuation of application No. 13/048,698, filed on Mar. 15, 2011, now Pat. No. 8,725,455.

(51) Int. Cl.
*G01N 29/00* (2006.01)
*F24F 3/16* (2006.01)
(Continued)

(52) U.S. Cl.
CPC ......... *G01M 99/005* (2013.01); *F24F 1/0071* (2019.02); *F24F 3/1603* (2013.01);
(Continued)

(58) Field of Classification Search
CPC ..... G01M 99/005; G01R 21/00; G01N 29/00; F24F 3/1603; F24F 2001/0096; F24F 2003/1682
See application file for complete search history.

(56) References Cited

U.S. PATENT DOCUMENTS

| 4,325,223 A | 4/1982 | Cantley |
| 6,342,840 B1 * | 1/2002 | Dunn .................... F25D 21/006 340/585 |

(Continued)

FOREIGN PATENT DOCUMENTS

| JP | 2001-099462 | 4/2001 |
| JP | 2005-282947 | 10/2005 |

(Continued)

OTHER PUBLICATIONS

Converting Percentages and Numerical Scores into Letter Grades, 2006, p. 1.*

(Continued)

*Primary Examiner* — Mohammad K Islam
(74) *Attorney, Agent, or Firm* — Loza & Loza, LLP; Anthony G. Smyth

(57) ABSTRACT

Systems and method for operating and monitoring refrigerators are described. Temperature cycles within the compartment are characterized using statistical, frequency and pattern analysis techniques to derive a steady-state characteristic of temperature within the compartment. A thermal sensor inside the conditioned area is monitored and temperature data sets can be analyzed to determine performance in comparison to a baseline, and energy consumption. Analysis of continuous temperature readings taken from individual or groups of freezers identifies patterns of variations in temperature cycles from which feedback on efficiency can be inferred. Electrical load can be determined by measuring or estimating current usage and identifying periods of time when compressors are active in the refrigerator.

25 Claims, 6 Drawing Sheets

(51) Int. Cl.
*F24F 1/00* (2019.01)
*G01M 99/00* (2011.01)
*G01R 21/00* (2006.01)
*F25D 29/00* (2006.01)
*F24F 1/0071* (2019.01)

(52) U.S. Cl.
CPC .......... *F25D 29/008* (2013.01); *G01N 29/00* (2013.01); *G01R 21/00* (2013.01); *F24F 2003/1682* (2013.01); *F25D 2600/06* (2013.01); *F25D 2700/12* (2013.01)

(56) References Cited

U.S. PATENT DOCUMENTS

| | | | | |
|---|---|---|---|---|
| 7,403,850 | B1* | 7/2008 | Boutin | G01M 15/05 701/107 |
| 8,121,818 | B2* | 2/2012 | Gorinevsky | G05B 23/0281 702/182 |
| 9,885,507 | B2* | 2/2018 | Pham | F25B 49/005 |
| 2003/0042861 | A1* | 3/2003 | Schwartz | H02P 29/02 318/434 |
| 2004/0210419 | A1* | 10/2004 | Wiebe | F25B 49/005 702/182 |
| 2005/0171645 | A1* | 8/2005 | Oswald | G05B 15/02 700/276 |
| 2005/0235660 | A1* | 10/2005 | Pham | F04C 28/00 62/126 |
| 2005/0244277 | A1* | 11/2005 | Hurst, Jr. | F04B 49/065 417/216 |
| 2006/0032245 | A1* | 2/2006 | Kates | F24F 3/1603 62/129 |
| 2006/0123807 | A1* | 6/2006 | Sullivan | G01D 4/004 62/129 |
| 2007/0156373 | A1* | 7/2007 | Yamashita | F24F 11/0086 702/182 |
| 2007/0220907 | A1* | 9/2007 | Ehlers | F25B 49/005 62/126 |
| 2008/0209925 | A1* | 9/2008 | Pham | F25B 49/005 62/126 |
| 2009/0037142 | A1* | 2/2009 | Kates | F25B 49/005 702/182 |
| 2009/0094998 | A1* | 4/2009 | McSweeney | F25B 49/005 62/129 |
| 2009/0119036 | A1* | 5/2009 | Jayanth | F04B 49/065 702/60 |
| 2009/0225479 | A1* | 9/2009 | Jayanth | G01R 19/10 361/30 |
| 2009/0255278 | A1* | 10/2009 | Taras | F25B 49/025 62/115 |
| 2009/0306820 | A1* | 12/2009 | Simmons | G07F 9/026 700/244 |
| 2010/0296914 | A1* | 11/2010 | Staroselsky | F04D 27/001 415/47 |
| 2011/0144944 | A1* | 6/2011 | Pham | F04C 28/00 702/182 |
| 2011/0184586 | A1* | 7/2011 | Asano | G05B 15/02 700/297 |
| 2011/0202293 | A1* | 8/2011 | Kobraei | G06Q 50/06 702/62 |
| 2011/0203538 | A1* | 8/2011 | Menier | B60H 1/00828 123/41.11 |
| 2011/0251807 | A1* | 10/2011 | Rada | G01D 4/00 702/61 |
| 2012/0049639 | A1* | 3/2012 | Besore | G01K 3/005 307/97 |
| 2012/0060526 | A1* | 3/2012 | May | F25D 29/00 62/115 |
| 2012/0210737 | A1* | 8/2012 | Giardino | F25D 29/00 62/115 |
| 2012/0218114 | A1* | 8/2012 | Davis | G01R 19/2513 340/646 |
| 2012/0318014 | A1* | 12/2012 | Huff | F25B 1/10 62/228.1 |
| 2013/0134102 | A1* | 5/2013 | Buchsbaum | A23L 2/70 210/703 |

FOREIGN PATENT DOCUMENTS

KR 10-20040088629 10/2004
KR 1020080040073 5/2008

OTHER PUBLICATIONS

PCT/US2011/028548. Int'l Search Report & Written Opinion (dated Oct. 31, 2011) 8 pp.

* cited by examiner

SYSTEMS AND METHODS FOR MONITORING, INFERRING STATE OF HEALTH, AND OPTIMIZING EFFICIENCY OF REFRIGERATION SYSTEMS

CROSS-REFERENCE TO RELATED APPLICATIONS

The present application is a continuation of U.S. patent application Ser. No. 13/048,698, filed Mar. 15, 2011, which is to issue as U.S. Pat. No. 8,725,455, and which claims priority from U.S. Provisional Patent Application No. 61/314,014 filed Mar. 15, 2010, which applications are expressly incorporated by reference herein for all purposes.

BACKGROUND OF THE INVENTION

Field of the Invention

The present invention relates generally to refrigeration systems and more particularly to systems and methods for monitoring the status, condition, performance and energy consumption.

Description of Related Art

Poor maintenance, misconfiguration or improper installation can result in wasted energy, decreased reliability and increased operational costs of refrigeration systems. Current maintenance practices entail frequent and costly inspections by trained technicians, or in rare instances, the installation of costly instrumentation to directly monitor the mechanical compressors and related components of the refrigeration system. Refrigeration equipment used in biomedical research, for example, typically goes through preventive maintenance inspections once every six months. Trained technicians perform manual inspections gathering performance data from each freezer to determine whether the refrigeration system requires additional maintenance. These inspections are labor intensive, costly and inefficient because the entire population of refrigeration systems must be inspected even though only a small percentage might require repair or maintenance.

One type of refrigeration system, Ultra Low Temperature (ULT) Freezers capable of maintaining storage temperatures of −80° C., are used extensively by research organizations and Life Science companies to store research specimens. The unexpected failure of a ULT Freezer or any refrigerated storage system in a life science application can result in the catastrophic loss of high-value, mission critical research specimens. To avoid loss, companies often adopt a policy calling for replacement of refrigeration systems after five years of service for lack of an affordable option to detect the onset of problems or failure.

Over time, all equipment suffers a loss of operating efficiency due to mechanical degradation, deferred maintenance or simple misconfiguration. According to US Government data, Life Science research and manufacturing facilities consume 2× to 8× more energy than commercial office buildings and "plug loads", energy consumed by equipment plugged into walls, consumes an estimated 20% to 45% of total energy used. For lack of an affordable and easy to deploy monitoring solution, these assets are "hidden" sources of wasted energy—energy that is 100% recoverable if affordable tools existed to manage them.

BRIEF SUMMARY OF THE INVENTION

Certain embodiments of the present invention comprise systems and methods for measuring and determining the status, health, performance, operating efficiency and energy consumption of the mechanical and electronic control systems of a refrigerator system by analyzing indirect indicators of status or performance, such as temperature in the storage compartment and other parameters. The refrigeration systems are monitored by wireless sensors which transmit data to an application server for evaluation. Data may be processed and plotted against time to form performance profiles for each freezer that can be represented with a mathematical function, such as a sine wave. The application server may be accessed through any web browser, and the user can have a distinct login identification and password. In certain embodiments, systems and methods are provided that assess efficiency and reliability issues associated with preventive maintenance, predicting when and what types of maintenance will need to be performed. The application can group and rank freezers according to their operating efficiency based on analysis and inferences drawn from their temperature profiles. The information may then be used to identify lower ranked freezers that require immediate or extensive service, based on measurements from sensors that have known correlations, and maintenance can be conveniently scheduled for lower ranked systems before they fail, while maintenance on higher ranked freezers can deferred with low risk and significant cost savings.

Other embodiments include methods for determining or inferring the electrical load drawn by an individual asset, such as a freezer, and tracking the location of one or multiple assets. In one embodiment, a single current reading for the entire circuit of multiple freezers can be taken periodically. Algorithms of the patterned behavior of multiple freezers can be formulated to the amount of current drawn through each unit that is connected in parallel. Patterned behavior can indicate which freezer is drawing an increased amount of current and becoming less efficient. In another embodiment, tracking the location of individual assets may be accomplished by magnetometer readings being transmitted to and processed by the application server. The user can view and manipulate a 3D map of one or multiple freezers.

DETAILED DESCRIPTION OF THE INVENTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration.

Certain embodiments of the present invention provide systems and methods for operating and monitoring refrigerators, including ULT freezers. Certain of the techniques described herein employ low cost, minimally invasive monitoring equipment that can identify operational characteristics of the monitored equipment and produces a range of performance measurements. Some of the performance measurements may be obtained indirectly. In one example, certain operational characteristics of commercial refrigeration systems may be determined by monitoring temperature cycles within a refrigerated compartment. Temperature cycles can be correlated to functional efficiency of compressors and other components.

For the purposes of this description, the state of health of a refrigeration system can be taken to include operational efficiency of thermodynamic cycles used for heat pumps and refrigerators. The state of health of the system may be used to diagnose specific causes of performance issues such as loss of a circulating refrigerant such as Freon, poor seals, inefficient or malfunctioning compressors, valves and other components. A current state of health may be assessed by comparing temperature cycles with plural baseline characteristics obtained from a broad sample of similar refrigeration systems.

Figure 1:
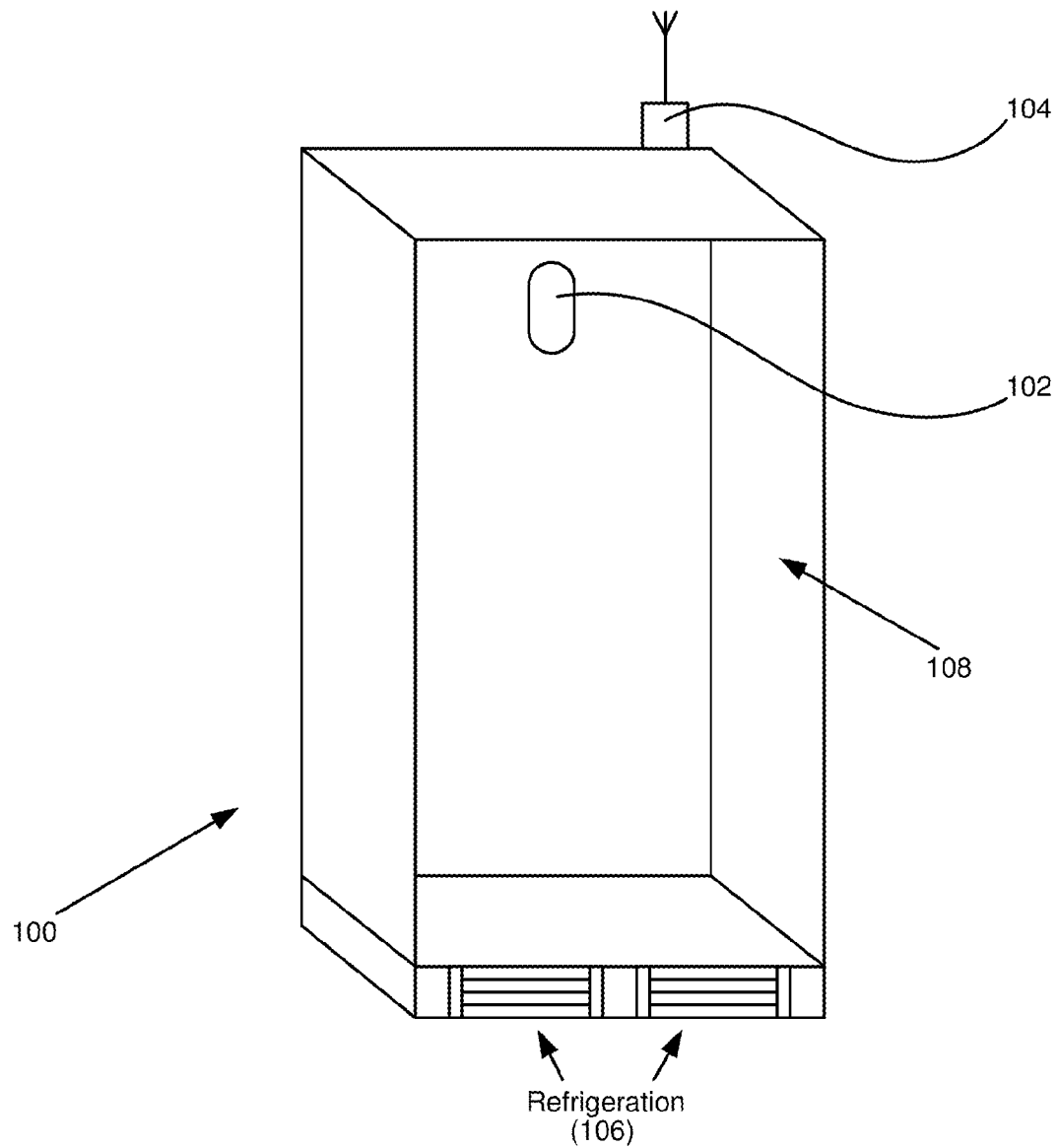
FIG. 1 illustrates a refrigeration unit subject to monitoring by the invention.

FIG. 1 is a simplified representation of a freezer 100 that is monitored according to certain aspects of the invention. The freezer 100 has an internal compartment, shown generally at 108 that is maintained at a desired temperature by a refrigeration device 106. For example, refrigeration device 106 may operate using a thermodynamic refrigeration cycle such as the Carnot cycle and may comprise one or more compressors, condensers, evaporators 106. Refrigeration device 106 may employ a charge of a refrigerant, such as Freon. It will be appreciated that a thermodynamic refrigeration cycle can serve as a refrigerator and/or as a heat pump. Accordingly, certain aspects of the present invention may be applied to heating and cooling systems. However, for the purpose of facilitating the appreciation of the presently disclosed inventions, a refrigeration device 106 will be assumed to operate using Freon in order to achieve deep cooling of a compartment 108 used to store items and materials which may include, for example, biological samples. It will be appreciated that the invention may be used in commercial food storage systems, consumer equipment and any other refrigeration system or system that uses a heat pump. In one example, an optimal and/or desired practical operating temperature for a ULT freezer is approximately −80° Celsius. The selection of operating temperature is typically made based on application requirements and operational limits of the refrigerant or other component of system 100. In the example of a ULT Freezer using a Freon refrigerant, the Freon-based thermodynamic cycle typically has a lower operating temperature limit of −86° Celsius.

It will be appreciated that the refrigeration device 106 may include plural component parts, some of which may be installed within and/or adjacent to compartment 108. Certain embodiments employ a thermally sensitive instrument 102, typically in thermal communication with the storage compartment 108, to measure temperature within a compartment 108 of freezer 100. Accordingly, at least a portion of instrument 102 may be provided within the compartment 108 to permit accurate measurements of temperature within compartment 108. Other methods for measuring temperature may be employed in accordance with certain aspects of the invention.

Thermally sensitive instrument 102 can be electrically or electromagnetically coupled to a controller 104, which is generally located outside the cooled interior of the refrigeration system 100, primarily to ensure an ambient temperature for electronics components that is within operational tolerances of electronics devices. Thermally sensitive instrument 102 typically comprises a thermal sensor 102, such as a thermocouple or thermometer and a controller 104 that can be mounted externally to the freezer 100. Certain refrigerators and freezers are manufactured with temperature measuring sensors installed in the compartment 108 and, in some embodiments, such sensors can serve as instrument 102.

Location of the controller 104 may be selected to facilitate access to power, for optimal wireless communication and/or for easy access during setup and maintenance. Controller 104 may include one or more processors, storage and means of communications as will be addressed in more detail below. Placement of the controller 104 on the outside of the freezer serves to ensure any contents inside of the compartment 108 will not damage the sensor 102 or inhibit transmission of the readings. In some embodiments, controller 104 may comprise a wireless transmitter. However, sensor 102 may employ hard-wired or other communication means instead of, or in addition to, a wireless transmitter. Controller 104 can be powered by internal battery and/or from an external power source or supply.

In certain embodiments, controller 104 may receive temperature measurements from one or more sensors 102 and may transmit accumulated temperature readings representing conditions within at least one compartment 108 over a predefined time interval. It is contemplated that some controllers 104 may be configured to relay temperature measurements without processing and/or may relay temperature measurements when contacted by another controller (not shown), gateway and/or accumulation device, regardless of the amount of data accumulated by the controller 104.

Figure 2:
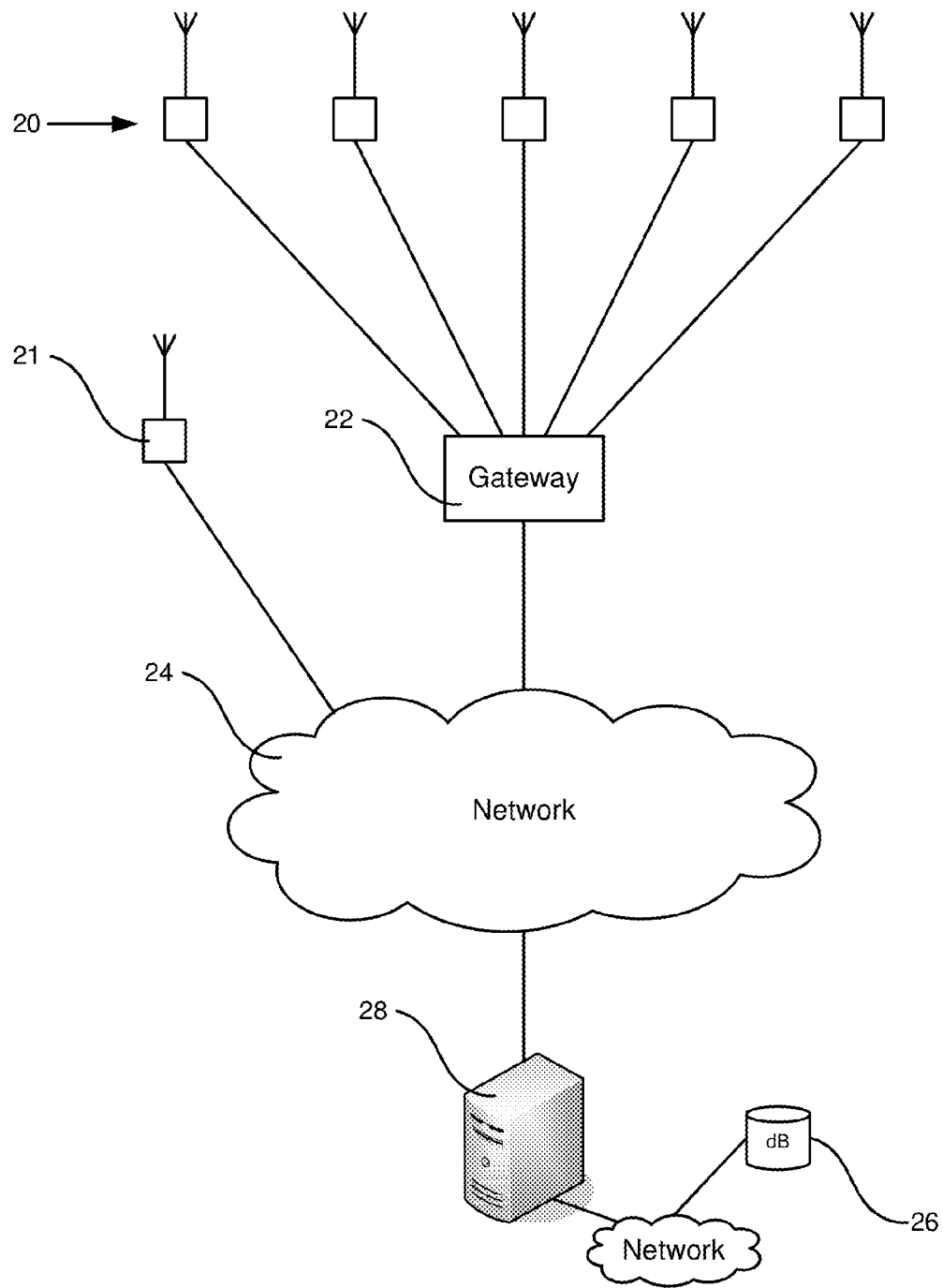
FIG. 2 illustrates possible options for the flow of data.

With reference to FIG. 2, temperature measurements can be sent from controllers 20, 21 via a network 24 to a processing system 28, which may include one or more computers and/or servers. Controllers 20 may provide information, including temperature measurements, to a gateway 22, to minimize complexity of each controller 20 and/or to improve communications efficiency. Gateway 22 can typically receive the data and may optionally pre-process the data into data sets which are then sent to an application server 28 for processing. In one example, gateway 22 packages 0 to 20measurements per device 20 into a data set for transmission through network 24. Application server 28 can comprise a database 26 such as, for example, a schemaless database.

In certain embodiments controller 21 may communicate directly with network 24 without an intervening gateway 22.

Typically, a controller 21 that can communicate directly with the network is configured to accumulate and order at least some measurements. Controller 20 or 21 may connect to network 24 using one or more repeaters, radio signal amplifiers, a mesh network and/or other sensors 20, 21 configured to perform relay functions. Accordingly, the range of sensor 20, 21 can be extended if the distance between the sensor 20 or 21 and the gateway 22 exceeds the transmission capabilities of the sensor 20 or 21. It will be appreciated that one or more sensors 20 or 21 may be connected to a wired network and may communicate with gateway 22 and/or server 28 using a LAN, WAN, Internet, Intranet, Extranet or other network. Moreover, a wired controller 21 may be configured in some embodiments to relay measurements transmitted wirelessly from other sensors.

Figure 3:
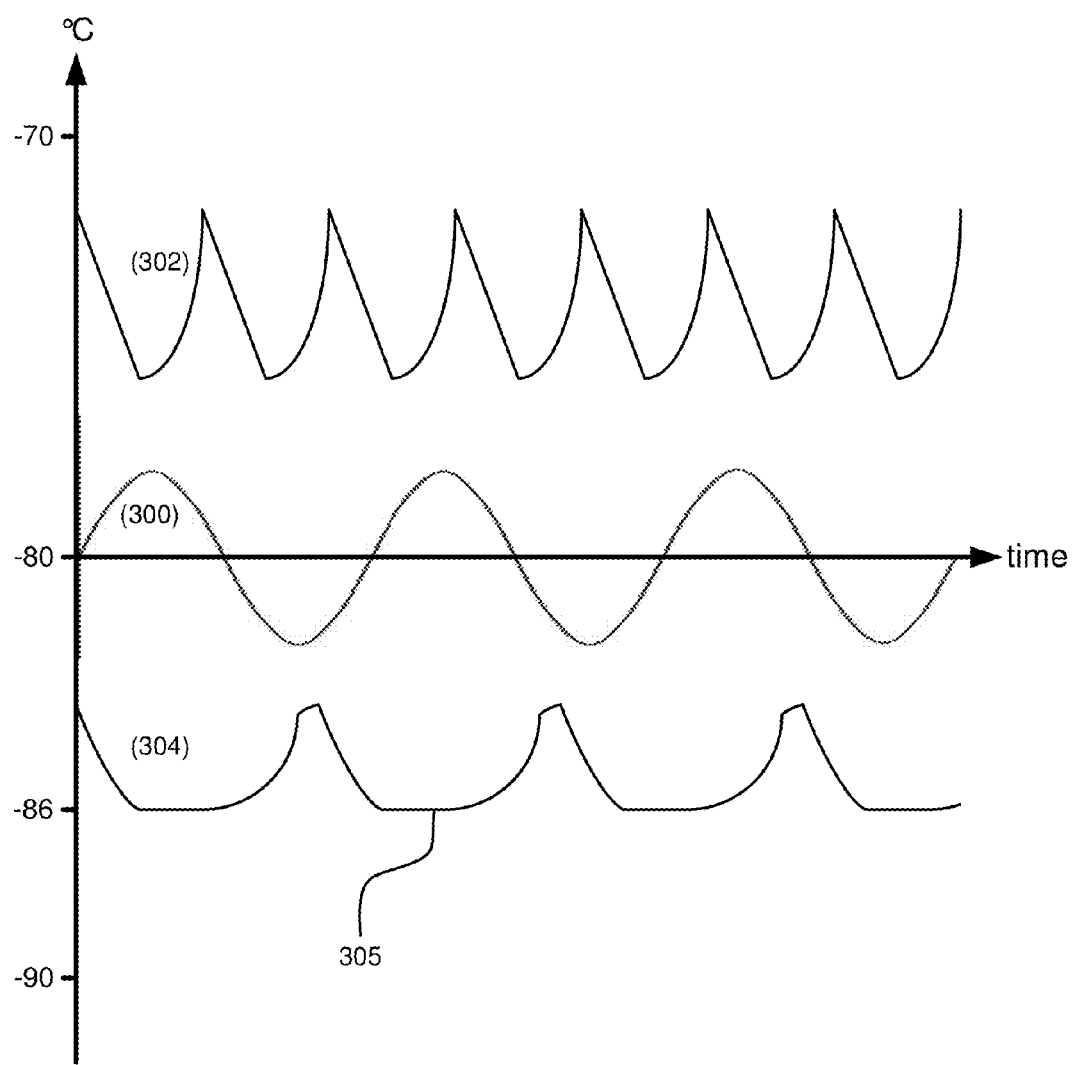
FIG. 3 temperature profiles for refrigeration units.

FIG. 3 depicts illustrative examples of profiles generated from temperature measurements for one type of refrigeration unit. These profiles are typically generated from temperature data captured over a period of time, and analysis of the temperature data can be used to determine freezer performance over the time period. Baseline profiles can be obtained as an aggregate of profiles of a plurality of similar freezers and/or from a freezer that is functioning within rated specifications. In particular, temperature cycles within the compartment can be characterized using statistical and pattern analysis techniques to derive a steady-state characteristic of temperature within the compartment.

A baseline value for a population of freezers of various manufacture and models can be established by comparing the plotted curves of each unit to one another in order to establish a normalized average pattern. A baseline can also be established using previously captured data obtained from a similar model freezer or group of freezers known to be running at nominal and/or optimal performance levels. Baseline data can be provided by a user and/or by download from a networked repository of baselines. Baseline data can be used for comparison with a temperature profile captured from an individual unit and the comparison may then yield information correlated to the health of the individual unit. Many approaches in establishing a baseline are conceivable, and some of these approaches may be user-defined. In certain embodiments, any appropriate comparison metric may be used. In one example, the comparison metric may comprise a statistical moving average.

In FIG. 3, an idealized and simplified baseline profile 300 of a freezer operating at optimal conditions is generally sinusoidal. The sine curve oscillates about −80° Celsius and has a consistent amplitude with minimum and maximum values of −84° Celsius and −76° Celsius, respectively. In this example, the refrigeration cycle may be considered to be active while the internal freezer temperature is greater than −80° Celsius and is disabled when the temperature is at, or below the nominal operating temperature of −80° Celsius. Because of thermal inertia within the freezer, temperature continues to change after the refrigeration cycle transitions between on and off. It will be appreciated that the volume and mobility of air within the freezer typically dictates the frequency of oscillation of temperature. Accordingly, the sample rate of temperature may be adjusted based on frequency of oscillation. Typically, at least two temperature readings per time period is required to capture frequency of oscillation, although more samples are generally required to identify the form of the curve, harmonic frequency content and step functions attributable to events, malfunction, etc.

Variations of maximum, minimum and median temperatures from nominal values, and/or shape of sections of the temperature characteristic can be used to assess the efficiency of the thermodynamic cycle and to indicate potential operational deficiencies of the refrigeration equipment. Temperature measurements can be analyzed and compare the freezer's performance to a baseline or stages during operation. Analysis of continuous temperature readings taken from individual freezers or groups of freezers can provide data or a pattern of temperature profiles that can be used to optimize power usage, schedule maintenance visits and generate alarms.

Signal analysis can be performed on a temperature profile using, for example, a statistical model. For example, a profile may indicate a peak representing a maximum temperature that terminates a rise from minimum to maximum values. The peak may be calculated as a statistical maximum. The profile may also indicate a minimum temperature terminating a fall in temperature as compartmental temperature is regulated. The minimum temperature may be calculated as a statistical minimum. In one example, the statistical maximum and minimum values may be calculated using a moving average. A statistical model can distinguish a true maximum and/or minimum temperature from other peaks and troughs in temperature identified within the profile. It will be appreciated that a variety of data filtering and analysis tools are known that can be applied to extract statistically significant characteristics of the profile. Such statistically significant characteristics can be used to manage freezer health.

The characteristics of a unit's temperature profile can be used to diagnose potential problems with refrigeration and other devices and can also be used to identify failing components. Advantageously, data can be obtained using wireless sensors from one or more refrigeration devices and the data can be characterized and categorized according to known correlations. As discussed above, the example of FIG. 3 provides a profile 300 representing a freezer operating at optimal conditions. FIG. 3 also shows a profile 304 that is a simplified example of compressor saturation when temperature within the freezer reaches the operational limit of Freon at −86° Celsius. It will be appreciated that profile 304 most likely represents a system in which the thermostat is set just above −86° Celsius and that the compressor continues to operate without effect until temperature within the freezer stabilizes at −86° Celsius or the temperature surrounding the thermostat reaches the set desired temperature. Clearly, the system represented by profile 304 is operating inefficiently because the compressor operates without producing useful work.

A profile 302 with a higher frequency, more rapid refrigeration cycles, in comparison to the baseline 300, might be attributed to an incorrectly calibrated freezer relative to its storage capacity. Observed temperatures that fall outside a range of internally calibrated temperature ranges may indicate one or more problems including, for example, a Freon leak through a valve or through a deteriorating seal, lack of Freon circulation due to a clogged capillary tube, an inefficient or damaged condenser fan, a clogged filter, obstructed condenser coils, worn compressor valves, and/or other mechanical failure. A greater amplitude of oscillation during a compressor cycle may indicate a transfer of energy between the freezer and the surroundings in the form of heat resulting in increased power usage. A rise in temperature results in more current being drawn through the unit. An irregular spike in temperature can indicate damaged insulation within the compressor coil. As discussed herein, deviations from a normal or ideal temperature characteristic can be correlated with dysfunctions of the cooling system 106, inadequate air circulation within the compartment 108 of refrigerator or freezer 100 (see FIG. 1). Correlations of dysfunction with observed temperature cycles are enabled in certain embodiments of the invention by observing, recording and analyzing temperature variations in a plurality of refrigeration devices over prolonged periods of time.

Figure 4:
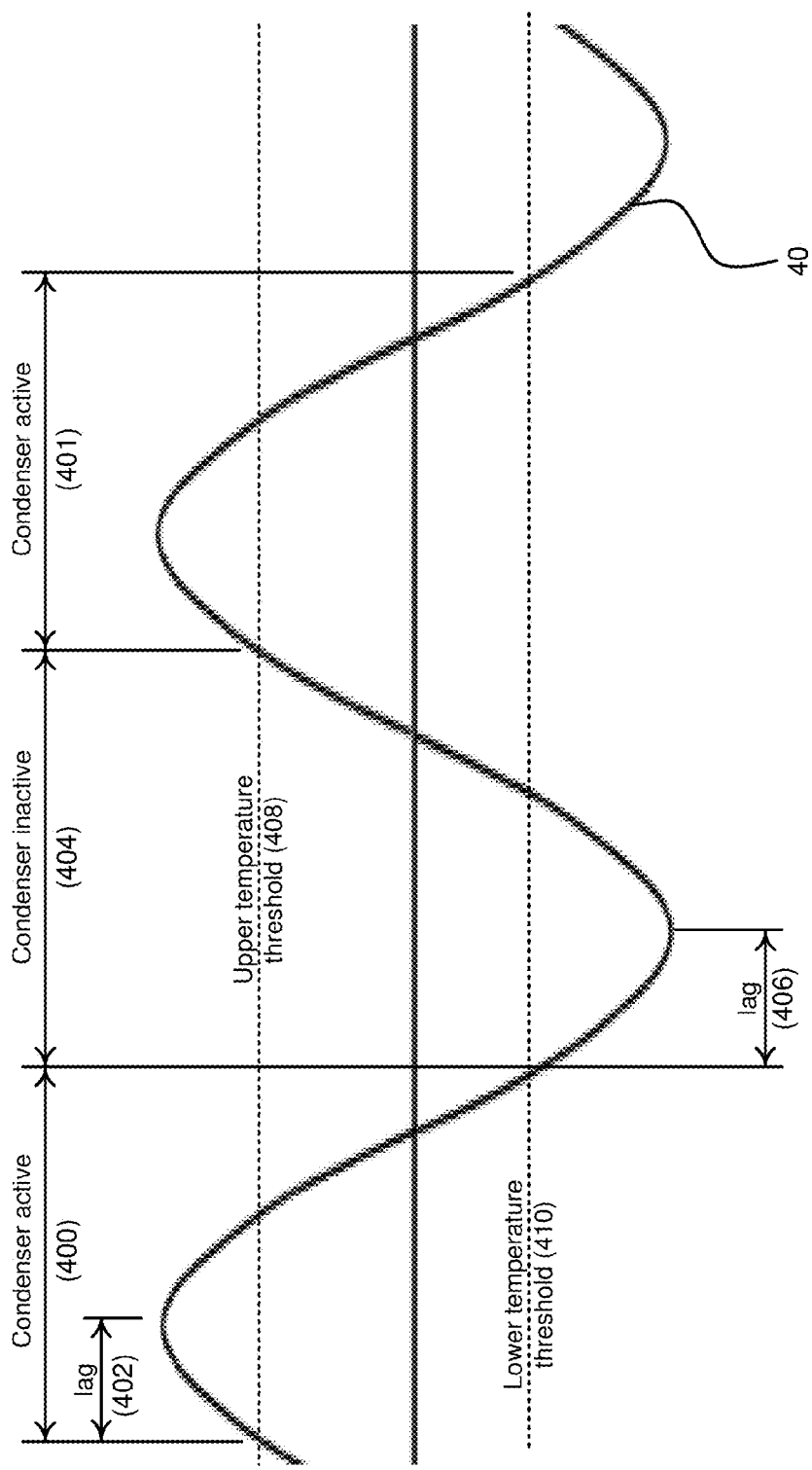
FIG. 4 illustrates the condenser cycle within a temperature profile.

FIG. 4 depicts an example of a temperature characteristic 40 of an idealized freezer compartment monitored according to certain aspects of the invention. The characteristic 40 identifies certain inferences that can be drawn regarding condenser and compressor cycles. As depicted, the characteristic is substantially sinusoidal having a phase shifted half-cycle 400 that corresponds to a period when the condenser of the freezer is active, followed by a half-cycle 404 when the condenser is inactive. Condensers function to cool the refrigerant, such as Freon, and convert the vapor into a liquid while at a constant temperature and pressure.

The phase shift between temperature characteristic 40 and the condenser half-cycles 400 and 404 can arises because of lags 402 and 406 in measured temperature response to compressor transitions between active and inactive, air flow within compartment 108 and for other reasons. In typical applications, condenser half-cycles 400 and 404 may be affected by other stages and characteristics of a refrigeration cycle, such as flash point evaporation and movement of the refrigerant through the evaporator. Transition between condenser half-cycles 400 and 404 may be correlated with a point in time before the highest temperature observed and corresponding to the crossing of an upper temperature threshold 408. Transition between condenser half-cycle 404 and next compressor active half-cycle 401 may be correlated with a point in time before the lowest temperature observed and corresponding to the crossing of a lower temperature threshold 410.

In certain embodiments, compressor activity can be inferred from the temperature characteristic 40. In the symmetric example of FIG. 4, temperature characteristic 40 is symmetric and phase shifts 402 and 406 can be assumed to have an equal length of time and effectively ignored. Therefore, it can be inferred that the condenser is turned on for 50% of the time. In other instances, the ratio of active and inactive condenser periods may be non-unitary and the resulting temperature characteristic is likely to non-sinusoidal but is likely to be periodic. Accordingly, signal analysis techniques may be employed in some embodiments to extract a fundamental frequency of the refrigeration cycle and to identify other cycles that can be attributed to condenser activity and inactivity. In some embodiments, analysis of the temperature characteristic may identify acceleration/deceleration of rate of change of temperature within a half cycle of the temperature characteristic; these changes in acceleration and/or deceleration, and general trends in the temperature characteristic before such changes can be used to identify compressor on/off transitions.

Other functions of a refrigerator may be identified from the temperature characteristic. For example, changes in the characteristic and/or the presence of certain harmonic frequencies may indicate when a pump is engaged, when refrigerant vapor is compressed and/or superheated. Long term changes in an observed temperature characteristic can be predictive of refrigeration system failure or loss of energy efficiency. For example, progressive deterioration of mechanical parts can lead to changes in the temperature characteristic (e.g. increased cycle frequency) that are detectable, given sufficient lapsed time. The rate of change and the manner of change can indicate impending loss of efficiency or failure based on similar changes previously observed other refrigeration devices.

It is also contemplated that the relationship between multiple connected compressors within a freezer can be identified by analysis of a temperature characteristic. In one example, the high pressure output stage of a first compressor can be coupled to the low pressure input stage of a second compressor. In another example, refrigeration systems may operate in parallel. Other refrigeration component combinations are contemplated. The relationship between the coupled compressors can be identified in a single temperature characteristic obtained from a freezer, while the state of health of each individual compressor in the combination may be inferred. As discussed herein, the cooling devices of some commercial refrigerators and freezers are instrumented such that direct temperature readings from compressors, evaporators and Freon lines may be obtained and used to augment temperature readings obtained from within the compartment 108. Such direct readings can be useful in isolating specific components in predictive failure analyses. Certain embodiments develop information regarding relationships between direct readings and measured compartment temperatures; such relationships may be used to identify problems with heat transfer elements and airflow with a compartment 108.

The attribution of potential problems to specific refrigeration units and/or component can be achieved in certain embodiments of the invention. In particular, the use of indirect temperature and/or electrical current measurements can determine the financial cost and benefit associated with each refrigeration unit. Measurement of electrical current can supplement cost/benefit analysis. For example, condenser activity may be accurately characterized for a plurality of freezers and such characterization may be used to estimate power usage, based on rated current usage of the condensers. However, a malfunctioning or laboring condenser may consume considerably more power than a nominally operating condenser. Therefore, in certain embodiments, the monitoring of a population of refrigeration/freezer devices can include measurement or estimation of electrical current usage and the effects of dysfunctional refrigeration components on power consumption. Information developed from such monitoring can be used to correlate electrical current readings to power consumption of condensers. For example, information from monitoring can be used to determine the amount of electrical current drawn by a condenser and the temperature characteristic for the refrigerator can be used to determine the amount of time that the condenser is active.

Electrical current usage of the condensers can be characterized for each individual freezer, for makes and models of freezer and can electrical current can be measured on a continuous or periodic basis. In certain embodiments, current measurements can be obtained for a freezer or refrigerator that is operating at designed efficiencies. These measurements can be correlated with temperature measurements for the refrigerator and freezer and can serve as a baseline for monitoring energy efficiency and for predicting failure.

Electrical current usage may be used to calculate power consumption by the refrigeration unit. The active power P required by a refrigeration unit operated at V volts and drawing I amps, is calculated as P=IV. Power used is then calculated as $PT_{ON}$ Watt Hours (typically stated as kilowatt hours), where $T_{ON}$ is the fraction of each temperature cycle when the compressor is active and drawing current. It will be appreciated that actual power usage may be obtained by scaling active power P with known power factors of the compressor or compressor type. Thus, calculation of power consumption by a freezer requires knowledge of current used by the refrigeration unit.

In certain embodiments, current load for an individual freezer may be determined or inferred, given that the power cycling properties of the freezer are predictable and/or determinable. In certain embodiments, electrical current measurements can be obtained for each refrigerator or freezer. In certain embodiments, current is measured at a power distribution panel, or on a power line that supplies current to multiple refrigerators and/or freezers. Baseline measurements of electrical current drawn through a circuit supplying two or more refrigeration units or freezers can be used to determine the load of each refrigeration unit or freezer. Given sufficient time and data points, a periodic measurement of current in a circuit that feeds plural freezers can provide sufficient information to discern the contributions of current use by each of the freezers. Typically, variations in current measured at the power source can be correlated with temperature characteristics measured simultaneously at each of the freezers, thereby attributing current usage by refrigeration unit or freezer.

Temperature and current correlations may be determined using a variety of techniques. In a simple example, when a temperature characteristic shows that a selected freezer is in a warming phase, it can be assumed that the selected freezer is drawing no current. When the selected freezer begins a cooling phase, any increase in measured electrical current may attributed to the selected freezer, if no other freezer has transitioned from "on to off" or from "off to on." Given sufficient data points, the individual contribution of each freezer can be calculated based on identified combinations of "on and off" freezers. It is frequently more convention to perform a frequency domain analysis of measured electrical current flow to find correlations with temperature cycles of refrigerators or freezers that receive the electrical current. In a simple example, if four freezers are provided electrical current from the same power outlet, and the compressors of the freezers operate at different frequencies, it would be sufficient to use a notch filter tuned to the frequency of a selected freezer to measure the amplitude of current attributable to the selected freezer. However, current and temperature data are typically analyzed using well-known signal analysis techniques.

Attribution of current consumption by individual freezers may include the use of various algorithms that identify variations in current usage over a refrigeration cycle and can provide an average electrical current flow and percentage "on" time for each compressor. Having determined electrical current usage and "on-time" for each refrigeration device, a user can determine power usage for each freezer over time, in comparison to other systems, and in comparison to benchmarks and/or nominal operating specifications. Thus, a single electrical current measurement device can provide insight into the efficiency of multiple systems. Indirect estimation of electrical current load drawn through an individual unit can also allow for a measurement of efficiency based on energy consumption when compared with a healthy unit.

In certain embodiments, methods for calculating power usage include measuring electrical current in a power line that supplies a plurality of freezers. Electrical current measurements are typically sampled at a sufficient rate to enable correlation of variations in electrical current flow with the characteristics of the individual freezers. A processor or controller can be configured to identify when each compressor is active, typically by analyzing the temperature characteristic for the freezer. At various sample points in time, a list of active compressors can be associated with a current measurement in the common power supply. With sufficient samples, the contribution of electrical current by each compressor can be calculated. This contribution represents electrical current consumed by the compressor and can be used to calculate the power consumption of the freezer based on the ratio of compressor active/inactive period. Accordingly, the efficiency of each freezer can be dynamically monitored.

In certain embodiments, a temperature sensor can recognize events relating to changes in temperature and respond by increasing sample rate. An application server may be configured to treat such increased sample rate as an alert for the corresponding freezer. It is contemplated that an alert may be triggered by any of a plurality of events, including detection of compartment temperature rising above one or more thresholds, temperature remaining above a maximum threshold for a predetermined amount of time, changes in rate of change of temperature and step changes in temperature. Similarly, alerts may be generated based on abnormal or sudden increase in current consumption. An alert related to temperature rising above a threshold can often be attributed to the door being opened. If the temperature readings remain at or exceed the maximum temperature, the freezer door may be been left open, and/or complete compressor failure may have occurred. Events may also include temperature range shifts from statistical norms for the freezer, often attributable to a failing or laboring compressor, incorrect calibration and/or changes in environmental conditions. For example, a compartment of a freezer may be overloaded given its storage capacity, and therefore unable to maintain a steady temperature. Alerts are typically sent to a user by Email, text message automated call, notification on a Web page and/or by any other suitable means.

Environmental changes may affect temperature readings and can include the specific placement of a freezer within a room adjacent to an unaccounted for heat sink. Freezers located near or by a window may display increases in temperature that correlate to a temperature increase due to time of day and/or seasonal weather. The temperature of the room or structure in which the freezer is housed may increase due to improperly functioning or set environmental controls. An increase in temperature readings can also correlate to an increase in current or power usage, as the compressor does more work to maintain compartment temperature. In certain embodiments, a collective efficiency metric can be calculated as power usage per area occupied by freezers. One such metric can be calculated as kWh/sq. ft. and the metric may be used to assess relative efficiency between different makes and models of freezers. The metric may also be used to set thresholds for performance such that a decrease in performance may trigger an alert, generate a service request, etc.

In certain embodiments, portions of data collected by temperature and/or electrical current sensors may be eliminated from consideration when characterizing operation of freezers, when identifying energy inefficiencies and for the purposes of predicting failure. It has been observed that most events, discontinuities and distortions in observed temperature characteristics can be attributed to human activity. Human activity that affects the temperature characteristic includes opening of the freezer or refrigerator, moving of the freezer or refrigerator, vibrations caused by human activity affecting airflow, variations in power supply due to use of electrical equipment and so on. Accordingly, analysis of data may be restricted to certain times of day when humans are not present. For example, freezers in commercial establishments may be monitored during early morning hours.

In certain embodiments, elements of the cooling system may be instrumented. For example, some commercially available freezers are shipped with temperature sensors installed in or around compressors, evaporators and conduits that carry Freon or other refrigerants. Typically, the temperature sensors are wired through a harness to one or more connectors for diagnostic and maintenance. In some embodiments, signals from these additional temperature sensors can be monitored by controllers provided according to certain aspects of the invention. The additional data derived from these signals can be analyzed to obtain additional baseline characteristics and to permit more precise identification of inefficiencies or dysfunction and to predict system failures. For example, temperature readings associated with various aspects of the cooling system can be used to characterize nominal and optimal cooling cycles.

In certain embodiments, a vibration sensor, such as a low frequency accelerometer, can detect vibration of a compressor. Compressor vibration normally occurs as a compressor is cycling on and/or off. The sensor can respond to changes in vibration patterns and/or can compare measured vibration to previously recorded or observed operating norms. Response may include an increased sampling rate which typically is interpreted by an application server as an alert. An alert may be processed when vibration occurs at an abnormal time interval. For example, a longer than normal vibration, or vibration at an unexpected time within the compressor cycle. Extended periods of observed vibration can provide a baseline for normal compressor function. In at least some embodiments, the vibration sensor may detect unusual vibrations that may be attributable to external events such as earthquakes or relocation of a freezer.

In certain embodiments, performance of freezers, compressors and alerts can be presented to users at a console or monitor. Users may access a monitoring system using an Internet application or browser, through a smartphone application, using a computer or tablet, or by any suitable system that supports user interactions with a networked console or control application. By means of a graphical user interface accessed via any Internet browser, user-specific data can be accessed from an application server 28 using a distinct login ID/password. Online macros may score the performance of each freezer. In one embodiment, a letter grade of A, B, C or F can be assigned to compare the unit with a baseline grade or peer performance. For example, freezers assigned a grade of C or F can be marked and shut down for preventive maintenance, while freezers rated with an A or a B grade may be allowed to remain in operation with no planned preventative maintenance.

If preventive maintenance is performed, a user, such as the service technician, can manually enter data into the online system. The user can track potential problems, allowing for intervention before failure occurs. Certain embodiments of the invention may also allow the user to select a logic function to predict future performance. This function can allow the user to input scenarios that project total cost of ownership for each system. The function can also calculate potential savings of economy, if, for example, F-grade freezers were to run at B-grade efficiency levels. By identifying systems with a low grade, total non-operational time for all systems, cost for repair, and risk to the materials being stored can be reduced.

Certain embodiments of the invention can map 2D images, such as a floor plan, of a structure to create a 3D representation of a freezer and other objects housed with varying elevation or user-defined region of the structure. A user can manipulate the 2D image(s), which can be reflected in pseudo-real time in the 3D structure, without the use of a separate animation software. The freezer(s) can be classified within a database to control for use and context, and a hierarchical relationship may be created to simplify management of the freezer(s) and structures. The freezer(s) may be displayed in a single view, including all units on all floors in a structure or multiple structures, or in discrete views by regions. Floors can also be hidden from view in order to simplify multi-floor structures. Certain embodiments can provide further details of a selected 3D view of a floor to be shown in a 2D map, in order to manage information and placement of objects. Other embodiments of the invention can enable the user to manipulate the 3D view, while the objects maintain position relative to an established coordinate system.

Figure 5:
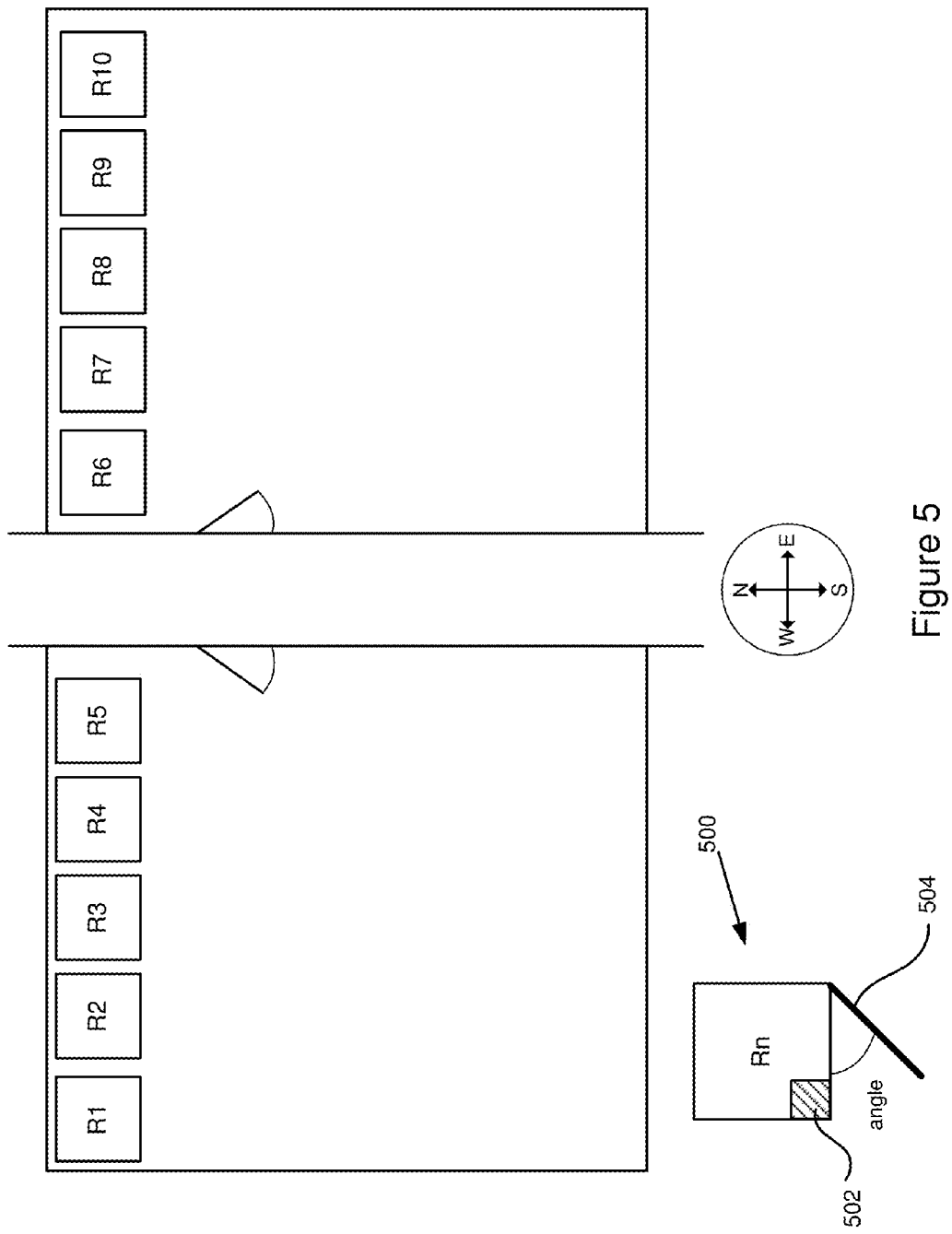
FIG. 5 illustrates the tracking embodiment of the invention.

Certain embodiments of the invention can also provide a means for monitoring and tracking the location of objects, such as a freezer or multiple freezers R1-R10 within different regions of a structure or in different structures, as shown in FIG. 5. Each freezer can be assigned a distinct icon, relevant identifying information, and strategically incorporated in a virtual layer. A distinct icon can indicate an alarm status by its changed color or an action, such as a spinning or revolving motion. For example, a freezer with an alarm status may be represented by a red icon and/or a spinning icon. In certain embodiments, animation of an icon may correlate to a specific event or type of alarm. For example, a rapidly spinning icon can represent a freezer with an observed increase in energy consumption. A red icon may represent a freezer that has been improperly (re)located within the structure. A blinking icon can represent a freezer while it is being moved.

For each freezer 500 (generally designated Rn), a device 502, such as a magnetometer, can be electrically connected to the temperature monitoring device and placed near the freezer door 504. Readings of a freezer's and/or freezer door's relative position can be transmitted to the application server 28 by an integrated transceiver or RF transmitter, which may be powered through the use of a current transducer, for example, an inductively coupled device, to utilize power from a voltage supply source to a compressor. The current transducer may also be used to a charge a battery, charge-pump circuit or power any device, display or attached integrated circuit. The information from the magnetometer can be used to determine the orientation of the freezer relative to a wall or structure and monitor when a freezer is moved from one location to another. Readings from the magnetometer can also indicate when the door is open and can account for irregularities in temperature data. Energy is added to the conditioned area when the door is opened and is not an indication of compressor performance to be used in the health analysis of the freezer. In addition to a temperature sensor, integrated transceiver, and current transducer, a comprehensive monitoring unit may also include additional attached digital input devices, such as an attached humidity sensor.

System Description

Figure 6:
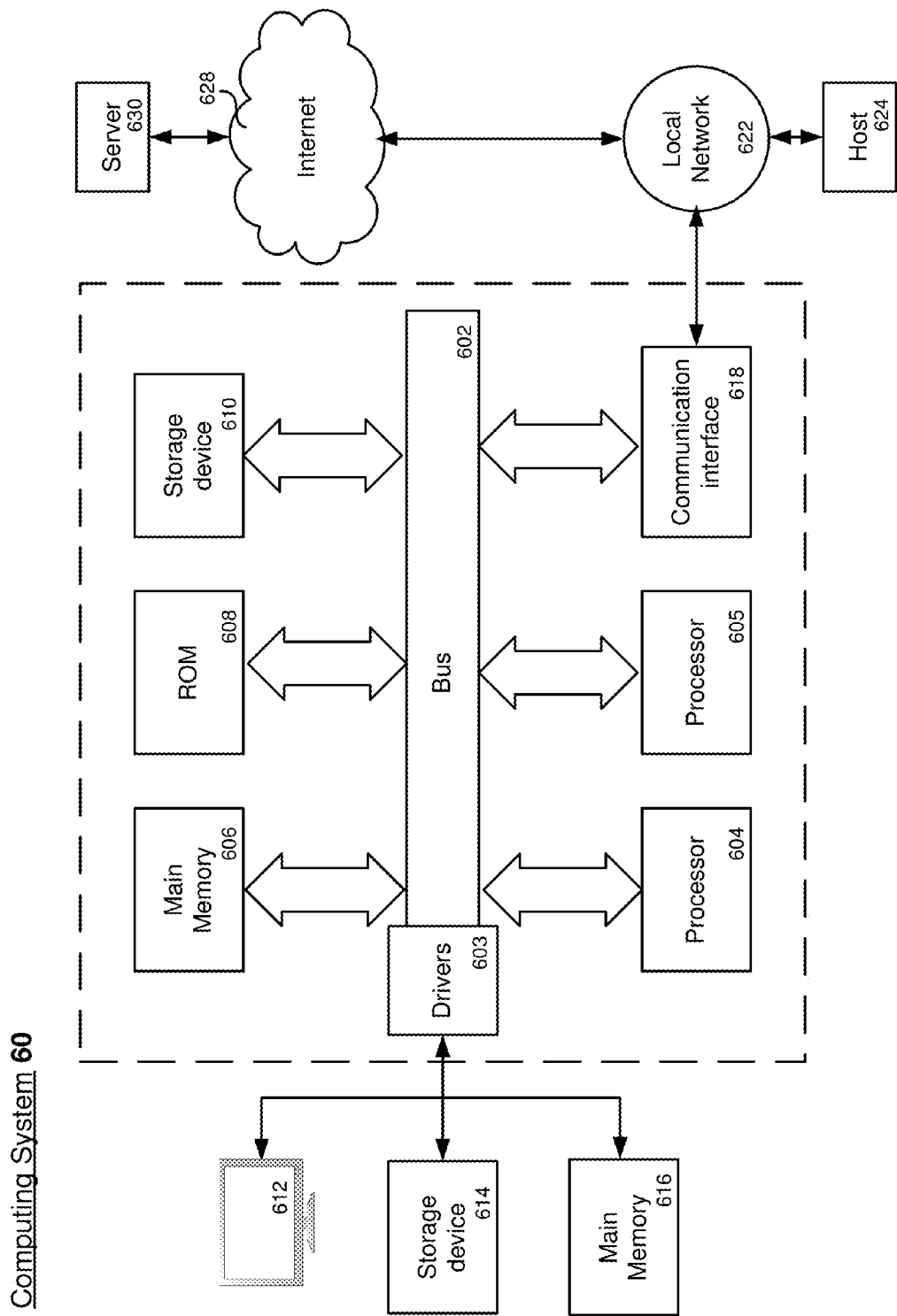
FIG. 6 is a simplified block schematic illustrating a processing system employed in certain embodiments of the invention.

Turning now to FIG. 6, certain embodiments of the invention employ a processing system that includes at least one computing system 60 deployed to perform certain of the steps described above. Computing systems may be a commercially available system that executes commercially available operating systems such as Microsoft Windows®, UNIX or a variant thereof, Linux, a real time operating system and or a proprietary operating system. The architecture of the computing system may be adapted, configured and/or designed for integration of some components in the processing system, for embedding in one or more of an image capture system, a manufacturing/machining system, a graphics processing workstation and/or a distributed network of devices. A typical computing system 60 may comprise a bus 602 and/or other mechanisms for communicating between processors, whether those processors are integral to the computing system 60 (e.g. 604, 605) or located in different, perhaps physically separated computing systems 60. Device drivers 603 may provide output signals used to control internal and external components.

Computing system 60 also typically comprises memory 606 that may include one or more of random access memory ("RAM"), static memory, cache, flash memory and any other suitable type of storage device that can be coupled to bus 602. Memory 606 can be used for storing instructions and data that can cause one or more of processors 604 and 605 to perform a desired process. Main memory 606 may be used for storing transient and/or temporary data such as variables and intermediate information generated and/or used during execution of the instructions by processor 604 or 605. Computing system 60 also typically comprises non-volatile storage such as read only memory ("ROM") 608, flash memory, memory cards or the like; non-volatile storage may be connected to the bus 602, but may equally be connected using a high-speed universal serial bus (USB), Firewire or other such bus that is coupled to bus 602. Non-volatile storage can be used for storing configuration, and other information, including instructions executed by processors 604 and/or 605. Non-volatile storage may also include mass storage device 610, such as a magnetic disk, optical disk, flash disk that may be directly or indirectly coupled to bus 602 and used for storing instructions to be executed by processors 604 and/or 605, as well as other information.

Computing system 60 may provide an output for a display system 612, such as an LCD flat panel display, including touch panel displays, electroluminescent display, plasma display, cathode ray tube or other display device that can be configured and adapted to receive and display information to a user of computing system 60. Typically, device drivers 603 can include a display driver, graphics adapter and/or other modules that maintain a digital representation of a display and convert the digital representation to a signal for driving a display system 612. Display system 612 may also include logic and software to generate a display from a signal provided by system 60. In that regard, display 612 may be provided as a remote terminal or in a session on a different computing system 60. For example, a temperature or other sensor may be controlled using a scaled down system that can be accessed by a mobile device or network system that can process image and other data under control of a controller, an operator, an administrator or other user. An input device 614 may be connected in some instances. Input device 614 may be provided locally or through a remote system and typically provides for alphanumeric input as well as cursor control 616 input, such as a mouse, a trackball, etc. It will be appreciated that input and output can be provided to a wireless device such as a PDA, a tablet computer or other system suitable equipped to display the images and provide user input.

According to one embodiment of the invention, data analysis may be performed by a remote computing system 60 and/or by a sensor controller and/or gateway device each having a processor 604 and/or 605. Processor 604 and/or 605 executes one or more sequences of instructions. For example, such instructions may be stored in main memory 606, having been received from a computer-readable medium such as storage device 610. Execution of the sequences of instructions contained in main memory 606 causes processor 604 to perform process steps according to certain aspects of the invention. In certain embodiments, functionality may be provided by embedded computing systems that perform specific functions wherein the embedded systems employ a customized combination of hardware and software to perform a set of predefined tasks. For example, controllers, sensors and gateways may communicate with a network using a predefined protocol, such as Zigbee, TCP/IP, etc. Thus, embodiments of the invention are not limited to any specific combination of hardware circuitry and software.

The term "computer-readable medium" is used to define any medium that can store and provide instructions and other data to processor 604 and/or 605, particularly where the instructions are to be executed by processor 604 and/or 605 and/or other peripheral of the processing system. Such medium can include non-volatile storage, volatile storage and transmission media. Non-volatile storage may be embodied on media such as optical or magnetic disks, including DVD, CD-ROM and BluRay. Storage may be provided locally and in physical proximity to processors 604 and 605 or remotely, typically by use of network connection. Non-volatile storage may be removable from computing system 60, as in the example of BluRay, DVD or CD storage or memory cards or sticks that can be easily connected or disconnected from a computer using a standard interface, including USB, etc. Thus, computer-readable media can include floppy disks, flexible disks, hard disks, magnetic tape, any other magnetic medium, CD-ROMs, DVDs, Blu-Ray, any other optical medium, punch cards, paper tape, any other physical medium with patterns of holes, RAM, PROM, EPROM, FLASH/EEPROM, any other memory chip or cartridge, or any other medium from which a computer can read.

Transmission media can be used to connect elements of the processing system and/or components of computing system 60. Such media can include twisted pair wiring, coaxial cables, copper wire and fiber optics. Transmission media can also include wireless media such as radio, acoustic and light waves. In particular radio frequency (RF), fiber optic and infrared (IR) data communications may be used.

Various forms of computer readable media may participate in providing instructions and data for execution by processor 604 and/or 605. For example, the instructions may initially be retrieved from a magnetic disk of a remote computer and transmitted over a network or modem to computing system 60. The instructions may optionally be stored in a different storage or a different part of storage prior to or during execution.

Computing system 60 may include a communication interface 618 that provides two-way data communication over a network (didn't see this labeled) that can include a local network 622, a wide area network or some combination of the two. For example, an integrated services digital network (ISDN) may used in combination with a local area network (LAN). In another example, a LAN may include a wireless link. Communication interface 618 typically provides data communication through one or more networks to other data devices. For example, communication interface 618 may provide a connection through local network 622 to a host computer 624 or to a wide are network such as the Internet 628. Local network 622 and Internet 628 may both use electrical, electromagnetic or optical signals that carry digital data streams.

Computing system 60 can use one or more networks to send messages and data, including program code and other information. In the Internet example, a server 630 might transmit a requested code for an application program through Internet 628 and may receive in response a downloaded application that provides for the anatomical delineation described in the examples above. The received code may be executed by processor 604 and/or 605.

Additional Descriptions of Certain Aspects of the Invention

The foregoing descriptions of the invention are intended to be illustrative and not limiting. For example, those skilled in the art will appreciate that the invention can be practiced with various combinations of the functionalities and capabilities described above, and can include fewer or additional components than described above. Certain additional aspects and features of the invention are further set forth below, and can be obtained using the functionalities and components described in more detail above, as will be appreciated by those skilled in the art after being taught by the present disclosure.

As discussed with reference to FIG. 1, thermally sensitive instruments 102 can be deployed in a plurality of refrigerators and freezers 100 to monitor compartment temperatures and to deduce characteristics of performance and efficiency for individual devices 100 and to predict failure or deterioration in performance. The characteristics are typically derived from information gathered over long periods of time, the information including temperature measurements gathered during that time. Other components of the information can optionally include measurements of electrical current for one or more devices 100, ambient temperatures of rooms that house devices 100, compressor/evaporator temperature measurements and other information obtained from other sensors mounted in device 100, detected exceptions such as freezer 100 door openings and so on. Observational and maintenance information can be provided by technicians dispatched to service machines, such information including readouts from control systems of device 100, diagnostic equipment, etc.

Temperature, electrical current and other measurements are typically obtained as samples, taken at a frequency calculated to capture fundamental periods of temperature change. Information obtained from each of the plurality of devices can be used to characterize the performance of the system 100 and may be stored as a set of raw measurements, as averaged characteristics of temperature, electrical current and power consumption. In some embodiments, the measurements may be subjected to a frequency domain analysis to obtain a set of parameters that describes the observed temperature and electrical current curves. Accordingly, the characteristics of a specific refrigerator may be stated as parameters that include a set of amplitudes of a fundamental frequency and its harmonics, one or more phase shifts and one or more transforms, such as a Fourier transform, a Laplace transform, or any other suitable transform. Such frequency domain representation may be particularly useful when seeking patterns in the characteristics of a device 100 and/or when matching temperature and electrical current measurements, especially where there are fewer current meters than freezers 100. Statistical analysis and other forms of data processing may be used for characterizing performance and identifying trends or patterns. In certain embodiments, digital signal processors may be used in the probe and/or monitoring system to generate frequency domain representations of temperature characteristics and/or current signals measured in a power line.

Baseline characteristics are typically developed for each brand and model of freezer 100. In certain embodiments, a baseline may be developed from one or more devices 100 that are known to be performing nominally. However, baseline performance can be obtained without using a known optimally performing device 100. Over time, and with a sufficient population of devices, a baseline may be extracted by identifying levels of performance (e.g. levels A, B, C E and F discussed herein) within the population of devices. Levels of performance may be assigned according to manufacturer specifications, user requirements, standards set by power companies or utility commissions, etc. Levels of performance may be used to determine eligibility for energy conservation rebates and the like and/or to identify candidates for replacement.

Baseline characteristics may be modified over time to reflect actual performance measurements that better reflect typical performance of a device 100 while in use. In use, performance of device 100 may be affected by the volume of materials stored in compartment 108, by the arrangement of stored materials and by the shape of packaging of stored materials. Performance of device 100 may also be affected by door openings, vibrations, changes in room temperature, and so on. As noted herein, it is often desirable to measure performance of device 100 at times when human interactions are minimized, for example, early morning or late evening. However, measurements taken at other times may be useful determining other performance characteristics, such as the time and energy required to restore operating temperatures after a disruption or discontinuity, such as an opened door. These other performance characteristics may useful in determining which type of device 100 should be used for long-term storage and which device 100 should be used when subject to frequent access.

It is to be expected that the performance characteristics of a refrigerator or freezer change over time, although such changes may be so gradual as to escape detection in conventional systems. In certain embodiments of the present invention, more recent characteristics, including temperature and electrical current cycles, may be compared with previously obtained baseline characteristics for a device 100. Changes detected over prolonged periods of time can be correlated with known patterns of change that are predictive of component or system failure, or predictive of performance degradation. In some instances, changes can simply indicate a need for maintenance. For example, a shortening of the period temperature cycle may indicate any of a number of conditions that cause the compressor to be active more frequently. However, rate of change of the period, step changes in the rate of change of the period, consistency or rate of change of the rate of change in period and changes in duty cycle (percentage of time compressor is turned on in a cycle) can provide additional data that may be used to diagnose the condition of the cooling system 100 and predict failure or loss of efficiency.

As discussed herein, performance characteristics are typically maintained for a variety of different types of refrigerators and freezers 100. Information derived from temperature and cooling cycles can be used to evaluate performance of different types of devices 100. For example, a metric can be developed that rates energy efficiency for different makes and models of devices used for refrigeration or freezing. In one example, energy efficiency may be rated as the cubic feet that can be maintained at a specified temperature or temperature range for each kilowatt-hour of energy expended. This metric permits evaluation of devices that have different compartment volumes, different compartment geometries, different shelf configurations, different cooling capacities, etc. Performance characteristics gathered in situ and real time may be used to evaluate performance of previously unseen devices 100 and to rate such performance against other similar or dissimilar devices. Such evaluations and ratings may be used to recommend to operators whether the device 100 should be replaced and may be used by utilities to determine eligibility for rebates.

Certain embodiments of the invention provide systems and methods for monitoring the operational health of a refrigeration system. Certain embodiments comprise a sensor operable to measure temperature within a compartment of the refrigeration system. Certain embodiments comprise a control processor in communication with the sensor and configured to receive a series of periodic temperature measurements from the sensor. In certain embodiments, the control processor is operable to communicate a sequence of temperature samples to a monitoring system that characterizes one or more operational aspects of the refrigeration system based on the sequence of temperature samples. In certain embodiments, each temperature sample comprises at least one of the series of periodic temperature measurements and information indicative of a corresponding time of measurement. In certain embodiments, the monitoring system is configured to predict operational dysfunctions of the refrigeration system based on an analysis of the one or more characterized operational aspects.

In certain embodiments, the characterized operational aspects comprise a temperature cycle measured within the compartment of the refrigeration system. In certain embodiments, the analysis of the characterized operational aspects includes a comparison of the temperature cycle with one or more baseline temperature cycles previously obtained from the refrigeration system. In certain embodiments, the analysis of the characterized operational aspects include a comparison of the temperature cycle with one or more baseline temperature cycles obtained from an optimally performing refrigeration system. In certain embodiments, the analysis of the temperature cycles includes a statistical analysis of the temperature cycle. In certain embodiments, the analysis of the temperature cycles includes a frequency-domain analysis of the temperature cycle. In certain embodiments, the analysis of the temperature cycles includes a pattern analysis of the temperature cycle.

In certain embodiments, the characterized operational aspects comprise a temperature cycle and a cycle of estimated electrical current consumed by the refrigeration system. In certain embodiments, the analysis of the characterized operational aspects includes estimating energy efficiency of the refrigeration system based on the estimated electrical current consumed by the refrigeration system. In certain embodiments, the current usage is calculated by cross-correlating a signal representative of estimated operating current of the refrigeration system with a signal representative of temperature measured within the compartment of the refrigeration system. Certain embodiments comprise a current transducer configured to measure current flow in an electrical circuit providing power to the refrigeration system. In certain embodiments, the characterized operational aspects comprise a temperature cycle and a cycle representing electrical current consumed by the refrigeration system. In certain embodiments, the analysis of the characterized operational aspects includes calculating energy efficiency of the refrigeration system based on the electrical current consumed by the refrigeration system. In certain embodiments, the electrical circuit provides power to a plurality of refrigeration systems. In certain embodiments, the monitor attributes a portion of the current flow to a selected refrigeration system based on an analysis of temperature cycles corresponding to the selected refrigeration system.

In certain embodiments, the monitor generates alerts in response to the identified dysfunctions. In certain embodiments, the identified dysfunctions including one or more of a temperature transition beyond nominal operating range, power usage beyond nominal operating ranges and a predicted failure of the refrigeration system. In certain embodiments, the characterized operational aspects comprise a temperature signal representative of the temperature within the compartment and a current signal representative of estimated electrical current consumed by the refrigeration system. In certain embodiments, the analysis of the characterized operational aspects includes an estimate of energy efficiency of the refrigeration system based on the estimated electrical current signal. In certain embodiments, the electrical current usage is calculated by cross-correlating the current signal with the temperature signal.

Certain embodiments comprise a current transducer configured to measure current flow in an electrical circuit providing power to the refrigeration system. In certain embodiments, the characterized operational aspects comprise a temperature signal and a signal representing electrical current consumed by the refrigeration system. In certain embodiments, the analysis of the characterized operational aspects includes calculating energy efficiency of the refrigeration system based on the electrical current signal. In certain embodiments, the electrical circuit provides power to a plurality of refrigeration systems, and wherein the monitor attributes a portion of the current flow to a selected refrigeration system based on a correlation of the temperature cycle with the current signal. In certain embodiments, the monitor generates alerts in response to the identified dysfunctions. In certain embodiments, the identified dysfunctions include one or more of a temperature transition beyond nominal operating range, power usage beyond nominal operating ranges and a predicted failure of the refrigeration system.

Certain embodiments of the invention provide methods for monitoring operational efficiency of a refrigeration system. Certain embodiments comprise generating a characteristic representing a time sequence of temperatures measured within a compartment of a refrigeration system. Certain embodiments comprise identifying differences between the characteristic and one or more baseline characteristics. In certain embodiments, the one or more baseline characteristics include at least one characteristic obtained from a nominally operating refrigeration system. Certain embodiments comprise determining one or more dysfunctions of a thermodynamic cycle based on the differences. In certain embodiments, the one or more dysfunctions includes a loss of energy efficiency, measured with respect to a baseline energy efficiency associated with the one or more baseline characteristics.

In certain embodiments, the one or more baselines include a previously obtained characteristic representing a time sequence of temperatures measured within a compartment of a refrigeration system. In certain embodiments, energy efficiency is measured as volume cooled for each unit of energy expended by the refrigeration system. In certain embodiments, the one or more dysfunctions include a predicted dysfunction, and further comprising identifying a corrective action to avert the predicted dysfunction. Certain embodiments comprise measuring electrical current in a power line that supplies the refrigeration system. In certain embodiments, measuring the electrical current in the power line includes determining the contribution of electrical current in the power line attributable to electrical current drawn by the refrigeration system. In certain embodiments, determining the contribution of electrical current attributable to the refrigeration system includes correlating changes in temperature of a storage compartment of the refrigeration system with variations of current measured in the power line.

Certain embodiments of the invention provide systems and methods for monitoring operational efficiency of a refrigeration system. Certain embodiments comprise a temperature sensor operable to measure temperature within a refrigerated compartment of the refrigeration system. Certain embodiments comprise a remote probe that samples temperature measurements provided at a configurable rate by the temperature sensor. Certain embodiments comprise a processor that generates a characteristic based on the sampled temperature measurements. In certain embodiments, the characteristic represents variations of temperature with time. In certain embodiments, the characteristic has a period, a maximum temperature and a minimum temperature. In certain embodiments, the processor is configured to identify operational inefficiencies of the refrigeration by comparing elements of the characteristic to elements of a plurality of baseline characteristics derived from one or more similar refrigeration systems.

In certain embodiments, the processor predicts failure of a component of the refrigeration system by identifying one or more differences between the elements of the characteristic and the elements of the plurality of baseline characteristics. Certain embodiments comprise a current transducer configured to measure current flow in an electrical circuit providing power to the refrigeration system. In certain embodiments, the processor generates a second characteristic representing electrical current consumed by the refrigeration system. In certain embodiments, the processor identifies a decline in energy efficiency of the refrigeration system over time. In certain embodiments, energy efficiency is measured as volume cooled for each unit of energy expended by the refrigeration system. In certain embodiments, the processor is identifies certain operational inefficiencies of the refrigeration by correlating elements of the characteristic with elements of a plurality of baseline characteristics derived from one or more similar refrigeration systems.

Certain embodiments of the invention provide systems and methods for monitoring the state of health of a refrigeration unit, such as a freezer, and inferring compressor performance by analysis of indirect temperature and current readings. A comprehensive monitoring unit may be comprised of a temperature sensor, accelerometer, circuitry, ammeter, magnetometer, integrated transceiver, current transducer, and additional attached digital input devices. Readings from a monitoring unit can be transmitted to an application server. In some of these embodiments, an application server may use a statistical model to perform signal analysis on temperature and current readings.

Certain embodiments of the invention provide systems and methods of monitoring operational efficiency of a refrigeration system. Some of these embodiments comprise obtaining a characteristic representing a time sequence of temperatures measured within a compartment of a refrigeration system. Some of these embodiments comprise identifying differences between the characteristic and one or more baseline characteristics. In some of these embodiments, the baseline characteristics include at least one characteristic obtained from a nominally operating refrigeration system. Some of these embodiments comprise determining one or more dysfunctions of a thermodynamic cycle based on the differences. Some of these embodiments comprise identifying a corrective action to optimize the operational efficiency of the refrigeration system.

Certain embodiments of the invention provide systems and methods for monitoring the operational health of a refrigeration unit. Some of these embodiments comprise a sensor configured to measure temperature within a compartment of the refrigeration unit. Some of these embodiments comprise a control processor in communication with the sensor and configured to receive periodic temperature measurements from the sensor. Some of these embodiments comprise data storage that maintains a history of temperatures comprising at least one temperature measurement obtained from the sensor. In some of these embodiments, the data storage further maintains information that identifies a time of measurement for each of the temperature measurements. In some of these embodiments, the control processor transmits the history of temperatures to a monitor that is configured to identify dysfunctions of the refrigeration unit based on analysis of a temperature cycle within the refrigeration unit.

In some of these embodiments, the analysis of the temperature cycles includes a comparison of the temperature cycle with one or more baseline temperature cycles obtained from a nominally performing refrigeration unit. In some of these embodiments, the analysis of the temperature cycles includes a comparison of the temperature cycle with one or more baseline temperature cycles obtained from an optimally performing refrigeration unit. Comparisons may be used to identify underlying patterns or cycles and other cycles or asymmetries that can be indicative of problems, inefficiencies, component malfunction or other dysfunctions that cause or lead to inefficiency and/or system failure. In some of these embodiments, the analysis of the temperature cycles includes a statistical analysis of the temperature cycle. For example, statistical analysis may be used to filter raw data to identify and exclude anomalous measurements and/or discontinuities, such as elevated temperature and recovery cycles associated with a door opening event. In some of these embodiments, the analysis of the temperature cycles includes a frequency analysis of the temperature cycle. Frequency analysis may be used to calculate a fundamental frequency of the temperature cycle that can be used to match an electrical current contribution to the refrigeration system. Frequency analysis may be used to obtain a transform that is used to characterize the cooling cycle of the refrigeration system. In some of these embodiments, the analysis of the temperature cycles includes a pattern analysis of the temperature cycle.

In some of these embodiments, the monitor estimates power usage of the refrigeration unit based on characteristics of the temperature cycle and current usage of the refrigeration unit. In some of these embodiments, the characteristics of the temperature cycle identify when the refrigeration unit is actively cooling. In some of these embodiments, the current usage is calculated based on estimated operating current of the refrigeration unit when the refrigeration unit is active.

Some of these embodiments comprise a current transducer configured to measure current flow in an electrical circuit providing power to the refrigeration unit. In some of these embodiments, the monitor calculates power usage of the refrigeration unit based on characteristics of the temperature cycle and the measured current flow. In some of these embodiments, the electrical circuit provides power to a plurality of refrigeration units. In some of these embodiments, the monitor attributes a portion of the current flow to one or more selected refrigeration units based on an analysis of characteristics of temperature cycles of the selected refrigeration units.

Some of these embodiments comprise a transducer and/or an accelerometer configured to identify motion, direction and orientation of the refrigeration unit. In some of these embodiments, the accelerometer detects vibration attributable to start up and shut down of the refrigeration unit. In some of these embodiments, a magnetometer indicates the orientation of a freezer relative to a wall or structure. In some of these embodiments, the monitor calculates power usage of the refrigeration unit based on the occurrence of vibration and current usage of the refrigeration unit. In some of these embodiments, the monitor generates alerts in response to the identified dysfunctions. In some of these embodiments, the identified dysfunctions include temperature transitions beyond nominal operating ranges. In some of these embodiments, the identified dysfunctions include power usage beyond nominal operating ranges. In some of these embodiments, the history of temperature is transmitted wirelessly.

Certain embodiments of the invention provide systems and methods for monitoring operational efficiency of a refrigeration system. Some of these embodiments comprise a temperature sensor provided within a refrigerated compartment of the refrigeration system. Some of these embodiments comprise a remote probe that records temperature measurements from the temperature sensor at a configurable rate. Some of these embodiments comprise a processor that extracts a characteristic from the temperature measurements. In some of these embodiments, the characteristic represents variations of temperature with time. In some of these embodiments, the characteristic having a period, a maximum temperature and a minimum temperature. In some of these embodiments, the processor is configured to identify operational inefficiencies of the refrigeration by comparing elements of the characteristic to elements of a plurality of baseline characteristics derived from one or more similar refrigeration systems.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

What is claimed is:

1. A method of monitoring operational efficiency of a refrigeration system, comprising:
   configuring a controller to collect data from one or more sensors, wherein the controller is located outside a cooled compartment of a monitored refrigeration system and communicatively coupled to the one or more sensors;
   receiving a plurality of measurements obtained by at least one sensor of the one or more sensors from an electric circuit providing power to the monitored refrigeration system, wherein the plurality of measurements is received from the controller over a connection established through a communication network, and wherein the plurality of measurements includes periodic measurements of current in a circuit that feeds the monitored refrigeration system over a period of time sufficient to characterize current usage during a plurality of temperature cycles within the cooled compartment of the monitored refrigeration system;
   determining a plurality of current usage cycles from the plurality of measurements, wherein each of the plurality of current usage cycles is indicative of electrical current consumed by a compressor of the monitored refrigeration system during the temperature cycle; and
   determining whether a failure or loss of energy efficiency of the monitored refrigeration system is predicted based on a trend detected in the plurality of current usage cycles that relate to variation from a nominal current usage cycle obtained by measuring current used by a nominally operating refrigeration system over a corresponding temperature cycle and a change in duty cycle in the plurality of current usage cycles.

2. The method of claim 1, wherein the at least one sensor comprises a current transducer.

3. The method of claim 1, wherein the nominal current usage cycle is included in a baseline characteristic that further includes information derived from specifications provided by a manufacturer of the refrigeration system.

4. The method of claim 3, wherein the baseline characteristic characterizes levels of performance associated with one or more devices.

5. The method of claim 3, wherein the baseline characteristic is modified over time to reflect performance measurements of the monitored refrigeration system obtained while the compressor is active.

6. The method of claim 1, further comprising:
   scoring performance of the refrigeration system based on differences between the plurality of current usage cycles and the nominal current usage cycle.

7. The method of claim 1, wherein differences between the plurality of current usage cycles and the nominal current usage cycle relate to a ratio of active periods and inactive periods of respective compressors.

8. The method of claim 1, wherein the monitored refrigeration system is marked for maintenance or shutdown when failure or loss of energy efficiency of the monitored refrigeration system is predicted.

9. The method of claim 1, wherein the one or more sensors comprise a vibration sensor coupled to the refrigeration system.

10. The method of claim 9, further comprising:
    receiving first measurements of vibration corresponding to compressor function and obtained by the vibration sensor; and
    determining whether a failure or loss of energy efficiency of the monitored refrigeration system is predicted by differences between the first measurements of vibration and second measurements of vibration obtained from the nominally operating refrigeration system.

11. The method of claim 1, wherein the trend relates to a rate of change of a period detected in the plurality of current usage cycles.

12. An apparatus, comprising:
    at least one processor;
    a memory coupled to the at least one processor; and
    a communication interface coupled to the at least one processor and configured to establish a connection with a controller through a communication network,
    wherein the at least one processor is configured to:
       configure the controller to collect data from one or more sensors, wherein the controller is located outside a cooled compartment of a monitored refrigeration system and communicatively coupled to the one or more sensors;

receive a plurality of measurements obtained by at least one sensor of the one or more sensors from an electric circuit providing power to the monitored refrigeration system, wherein the plurality of measurements is received from the controller over the connection established through the communication network, and wherein the plurality of measurements includes periodic measurements of current in a circuit that feeds the monitored refrigeration system over a period of time sufficient to characterize current usage during a plurality of temperature cycles within the cooled compartment of the monitored refrigeration system;

determine a plurality of current usage cycles from the plurality of measurements, wherein each of the plurality of current usage cycles is indicative of electrical current consumed by a compressor of the monitored refrigeration system during the temperature cycle; and determine whether a failure or loss of energy efficiency of the monitored refrigeration system is predicted based on a trend detected in the plurality of current usage cycles that relate to variation from a nominal current usage cycle obtained by measuring current used by a nominally operating refrigeration system over a corresponding temperature cycle and a change in duty cycle in the plurality of current usage cycles.

13. The apparatus of claim 12, wherein the at least one sensor comprises a current transducer.

14. The apparatus of claim 12, wherein the at least one processor is configured to:

score performance of the refrigeration system based on differences between the plurality of current usage cycles and the nominal current usage cycle, wherein scored performance is used to determine whether the refrigeration system is marked for maintenance, shutdown, or replacement.

15. The apparatus of claim 12, wherein the at least one processor is configured to:

receive first measurements of vibration corresponding to compressor function and obtained by a vibration sensor coupled to the refrigeration system; and determine whether a failure or loss of energy efficiency of the monitored refrigeration system is predicted by differences between the first measurements of vibration and second measurements of vibration obtained from the nominally operating refrigeration system during the temperature cycle.

16. The apparatus of claim 15, wherein the first measurements of vibration correspond to a period of observed vibration measured by the vibration sensor.

17. The apparatus of claim 12, wherein the trend relates to a rate of change of a period detected in the plurality of current usage cycles.

18. A non-transitory computer-readable storage medium having instructions stored thereon including instructions that, when executed by a processor, cause the processor to:

configure a controller to collect data from one or more sensors, wherein the controller is located outside a cooled compartment of a monitored refrigeration system and communicatively coupled to the one or more sensors;

receive a plurality of measurements obtained by at least one sensor of the one or more sensors from an electric circuit providing power to the monitored refrigeration system, wherein the plurality of measurements is received from the controller over a connection established through a communication network, and wherein the plurality of measurements includes periodic measurements of current in a circuit that feeds the monitored refrigeration system over a period of time sufficient to characterize current usage during a plurality of temperature cycles within the cooled compartment of the monitored refrigeration system;

determine a plurality of current usage cycles from the plurality of measurements, wherein each of the plurality of current usage cycles is indicative of electrical current consumed by a compressor of the monitored refrigeration system during the temperature cycle; and determine whether a failure or loss of energy efficiency of the monitored refrigeration system is predicted based on a trend detected in the plurality of current usage cycles that relate to variation from a nominal current usage cycle obtained by measuring current used by a nominally operating refrigeration system over a corresponding temperature cycle and a change in duty cycle in the plurality of current usage cycles.

19. The storage medium of claim 18, wherein the plurality of measurements includes measurements provided by a current transducer.

20. The storage medium of claim 18, wherein the nominal current usage cycle is included in a baseline characteristic that includes measured levels of performance associated with one or more devices.

21. The storage medium of claim 20, wherein the baseline characteristic includes information derived from specifications provided by a manufacturer of the refrigeration system.

22. The storage medium of claim 20, wherein the instructions cause the processor to:

update the baseline characteristic to reflect performance measurements of the refrigeration system obtained while the refrigeration system is in use.

23. The storage medium of claim 18, wherein the instructions cause the processor to:

score performance of the refrigeration system based on differences between the plurality of current usage cycles and the nominal current usage cycle; and determine whether the refrigeration system is to be identified for maintenance, shutdown or replacement based on the scored performance.

24. The storage medium of claim 18, wherein the instructions cause the processor to:

receive first measurements of vibration corresponding to compressor function and obtained by a vibration sensor coupled to the refrigeration system; and determine whether a failure or loss of energy efficiency of the monitored refrigeration system is predicted by differences between the first measurements of vibration and second measurements of vibration obtained from the nominally operating refrigeration system during the temperature cycle.

25. The storage medium of claim 18, wherein the trend relates to a rate of change of a period detected in the plurality of current usage cycles.

* * * * *